United States Patent
Wang et al.

(10) Patent No.: US 8,790,536 B2
(45) Date of Patent: Jul. 29, 2014

(54) METAL ETCHING METHOD, METAL ETCHING CONTROL METHOD AND CONTROL DEVICE THEREOF

(75) Inventors: Chin-wen Wang, Shenzhen (CN); Chengming He, Shenzhen (CN)

(73) Assignee: Shenzhen China Star Optoelectronics Technology Co., Ltd., Shenzhen, Guangdong Province (CN)

(*) Notice: Subject to any disclaimer, the term of this patent is extended or adjusted under 35 U.S.C. 154(b) by 163 days.

(21) Appl. No.: 13/219,696

(22) Filed: Aug. 28, 2011

(65) Prior Publication Data

US 2012/0132621 A1    May 31, 2012

(30) Foreign Application Priority Data

Nov. 30, 2010 (CN) .......................... 2010 1 0571447

(51) Int. Cl.
*C03C 15/00* (2006.01)
(52) U.S. Cl.
USPC .................. 216/100; 216/13; 216/37; 216/83
(58) Field of Classification Search
USPC ......... 216/13, 37, 83, 100, 88; 252/79.1–79.4
See application file for complete search history.

(56) References Cited

U.S. PATENT DOCUMENTS

| 6,798,529 B2* | 9/2004 | Saka et al. ................ 356/630 |
| 6,897,964 B2* | 5/2005 | Takahashi et al. .......... 356/503 |
| 2008/0041813 A1 | 2/2008 | Oladeji et al. |

FOREIGN PATENT DOCUMENTS

| CN | 2112206 U | 8/1992 |
| CN | 1480995 A | 3/2004 |
| CN | 1574245 A | 2/2005 |
| JP | 2004186289 A | 7/2004 |

OTHER PUBLICATIONS

Marvin Brent et al. Global Semiconductor Manufacturing Technology (2003) pp. 1-4.*
Naresh Chand et al. Joural of Electrochemical Society, Voi. 140, No. 3, Mar. 1993, pp. 703-705.*

* cited by examiner

*Primary Examiner* — Nadine Norton
*Assistant Examiner* — Maki Angadi
(74) *Attorney, Agent, or Firm* — Cheng-Ju Chiang

(57) ABSTRACT

Disclosed is a metal etching method, a metal etching control method and a control device thereof. The metal etching control method is employed in a metal wet etching machine and comprises steps below: performing etching to a metal film and acquiring an etching end time of the metal film; multiplying the etching end time with a constant ratio to acquire the over etching time of the metal film; and performing etching to the metal film with the over etching time to complete the etching to the metal film. The present invention can precisely judge a total real etching time needed for each of a batch of metal films as performing metal etching to the metal films to reduce the issue of unstable etching qualities as the metal film thicknesses are not regular.

7 Claims, 6 Drawing Sheets conveying direction of substrate

METAL ETCHING METHOD, METAL ETCHING CONTROL METHOD AND CONTROL DEVICE THEREOF

BACKGROUND OF THE INVENTION

1. Field of the Invention

The present invention generally relates to a metal etching method, a metal etching control method and a control device thereof, and more particularly to a metal etching method, a metal etching control method and a control device thereof which can precisely judge a total real etching time needed for each of a batch of metal films as performing metal etching to the metal films.

2. Description of Prior Art

Please refer to FIG. 1, which shows a diagram of that a substrate 100 carrying a metal film is conveyed in a metal wet etching machine 1 when LCD panel is manufactured. In the LCD panel manufacture, the metal wet etching machine 1 is used for executing a wet etching to the metal film. The metal wet etching process is to load the substrate 100 carrying the plated metal film (metal layer) in an etching bath full of acid solution. Then, etching is performed to the area unprotected by the photoresist to obtain the patterns protected by the photoresist. Before the metal wet etching machine 1 is used to perform etching to a batch of metal films. One in the batch of the metal films is selected as being a sample metal film and to acquire an etching end time of the sample metal film. Two ways of performing the etching end time detection exist in the industry nowadays. One is shown in FIG. 2, which shows a diagram of that a work 150 executes a random check for judging the etching end time of the metal films with unaided eye by experience according to prior art. The other is to acquire the etching end time of the sample metal film through the sensor 104 of the EPD (End Point Detector). The etching end time is defined as the period of time from loading the substrate 100 into the etching bath full of acid solution till the sensor of the end point detector detects the metal film penetrated by the light (the substrate 100 is employed for carrying the metal film). The working theory of the end point detector is based on the light reflection/penetration. As the metal film remains on the substrate 100, the light generated by the sensor of the end point detector is still reflected by the metal film because the light cannot penetrate the metal film. The end point detector judges that the end point time of the metal film has not arrived hereby; as the metal film carried by the substrate 100 is etched completely, the light generated by the sensor of the end point detector can penetrate the substrate 100 and is not be reflected because the light can penetrate the substrate 100. The end point detector judges that the end point time of the metal film has arrived hereby.

After the etching end time is acquired, the etching is now performed to the batch of the metal films. To prevent the situation of unequal etching rates and the remaining metal film, generally, an over etching time is added on after the etching end time, which is a total real etching time. The definition is: total real etching time=etching end time+(etching end time×over etching ratio) to prevent the situation of remaining metal film. For example, the acquired end point time of the metal film is 100 sec, and the setting ratio is 42%. Then, the total real etching time for each of the metal films is set at 142 sec.

However, some drawbacks still exist in the aforesaid method. Among the batch of the metal films, it is impossible that all the thicknesses of the metal films are the same. Under such circumstance, if the etching with the same total real etching time is performed to each of the metal films, the thinner metal film will be over etched and the thicker metal film will not be etched enough and consequently results in the unstable etching quality.

Therefore, there is a need to provide a metal etching method, a metal etching control method and a control device thereof for solving the existing drawbacks of aforementioned prior art.

SUMMARY OF THE INVENTION

An objective of the present invention is to provide a metal etching method, a metal etching control method and a control device thereof which is capable of precisely judging a total real etching time needed for each of a batch of metal films as performing metal etching to the metal films.

For realizing the aforesaid objective of the present invention, the present invention provides a metal etching method, employed in a metal wet etching machine and comprises steps below: performing etching to a metal film and acquiring an etching end time of the metal film; multiplying the etching end time with a constant ratio to acquire the over etching time of the metal film; and keeping performing etching to the metal film with the over etching time to complete the etching to the metal film.

In one embodiment of the present invention, the step of acquiring the etching end time of the metal film is that the metal wet etching machine acquires the etching end time from an end point sensor.

In one embodiment of the present invention, the step of multiplying the etching end time with the constant ratio is executed by the metal wet etching machine or the end point sensor.

In one embodiment of the present invention, the step of acquiring the etching end time of the metal film is that the metal wet etching machine performs end point detection to the metal film to acquire the etching end time.

In one embodiment of the present invention, the step of multiplying the etching end time with the constant ratio is executed by the metal wet etching machine.

In one embodiment of the present invention, the end point sensor is located inside the metal wet etching machine for detecting the etching end time of the metal film during the etching.

In one embodiment of the present invention, the constant ratio is 42%.

For realizing the aforesaid objective of the present invention, the present invention provides a metal etching control method, employed in a metal wet etching machine and comprises steps below: acquiring an etching end time of the metal film; acquiring an over etching time of the metal film according to the etching end time and a preset algorithm; and delivering the over etching time to the metal wet etching machine for performing etching to the metal film with the over etching time to complete the etching to the metal film.

In one embodiment of the present invention, the preset algorithm is to multiply the etching end time with a constant ratio to acquire the over etching time.

In one embodiment of the present invention, the preset algorithm is to multiply the etching end time with a first ratio to acquire the over etching time, and the first ratio is a sum of a constant ratio plus an extra necessary fixed ratio, which is presupposed according to the metal film etching times performed by the metal wet etching machine.

In one embodiment of the present invention, the preset algorithm is to multiply the etching end time with a second ratio to acquire the over etching time, and the second ratio is a sum of a constant ratio plus an extra percentage, which is presupposed according to the increase of the etching end times. The extra percentage is an extra linear increasing percentage, an arithmetic series percentage or a geometric series percentage.

For realizing the aforesaid objective of the present invention, the present invention provides a metal etching control device, comprising: a first acquiring module, acquiring an etching end time of the metal film; a second acquiring module, acquiring an over etching time according to the etching end time and a preset algorithm; and a delivering module, delivering the over etching time to a metal wet etching machine for performing etching to the metal film with the over etching time to complete the etching to the metal film.

In one embodiment of the present invention, the first acquiring module is an end point sensor.

In one embodiment of the present invention, the first acquiring module is located inside the metal wet etching machine for detecting the etching end time of the metal film during the etching.

In one embodiment of the present invention, the preset algorithm is to multiply the etching end time with a constant ratio to acquire the over etching time.

According to the metal etching method, the metal etching control method and the metal etching control device of the present invention, the total real etching time needed for each of a batch of metal films can be precisely judged as performing metal etching to the metal films. The issue of unstable etching qualities as the metal film thicknesses are not regular can be reduced to promote the yield of the LCD panel manufacture.

DETAILED DESCRIPTION OF THE INVENTION

Detail descriptions of the specific embodiments of the adjustment method of the LCD overdrive voltage and the device thereof provided by the present invention in conjunction with the attached figures are introduced below.

Figure 1:
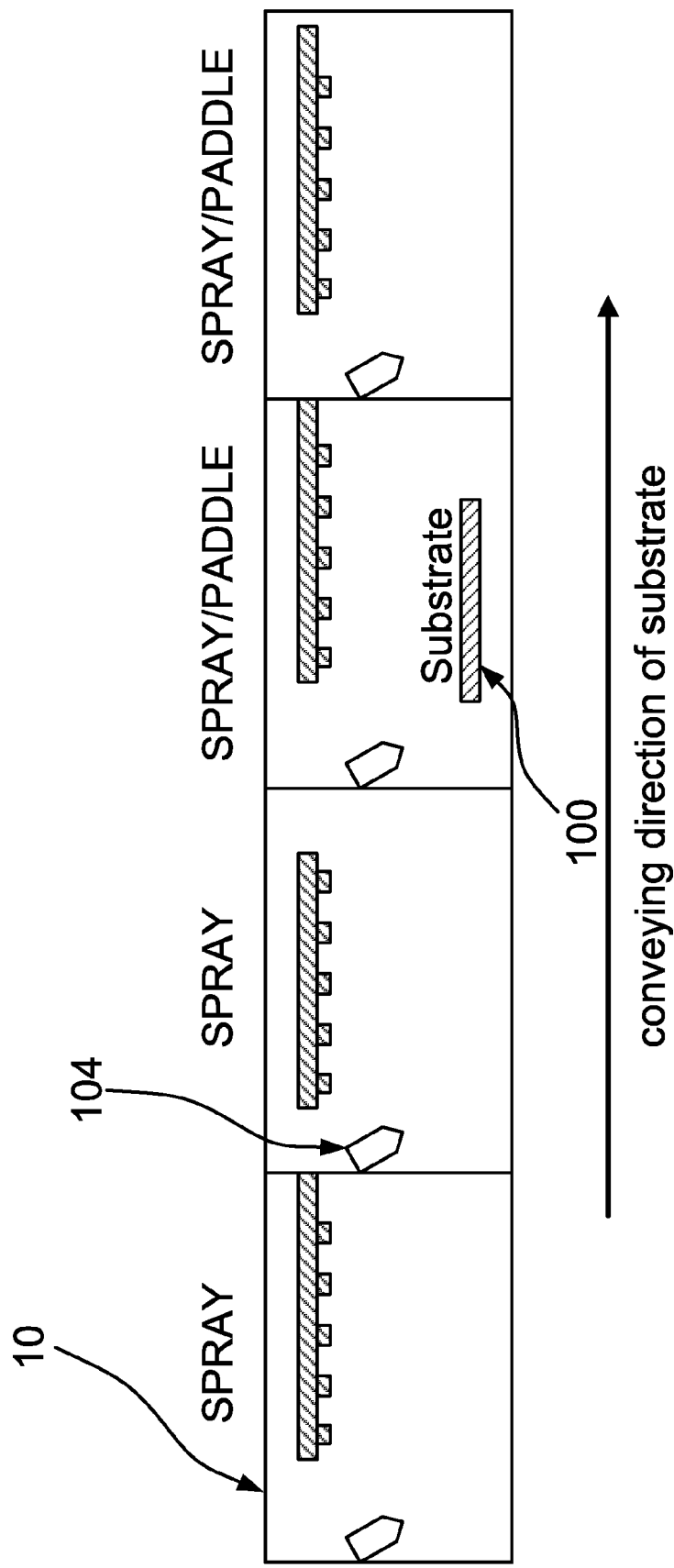
FIG. 1 shows a diagram of that a substrate carrying a metal film is conveyed in a metal wet etching machine when LCD panel is manufactured.
Figure 2:
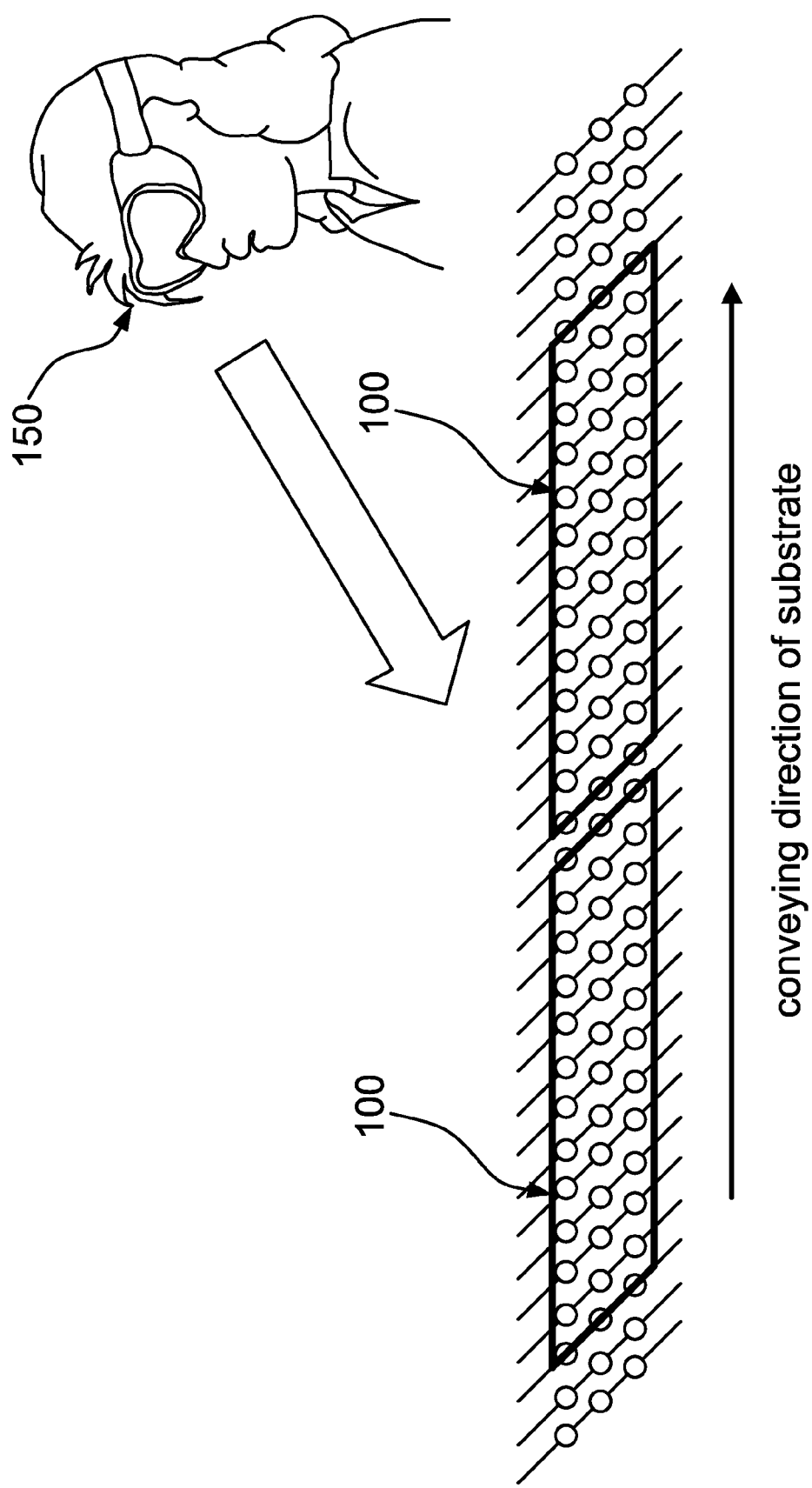
FIG. 2 shows a diagram of that a work executes a random check for judging the etching end time of the metal films with unaided eye according to prior art.
Figure 3:
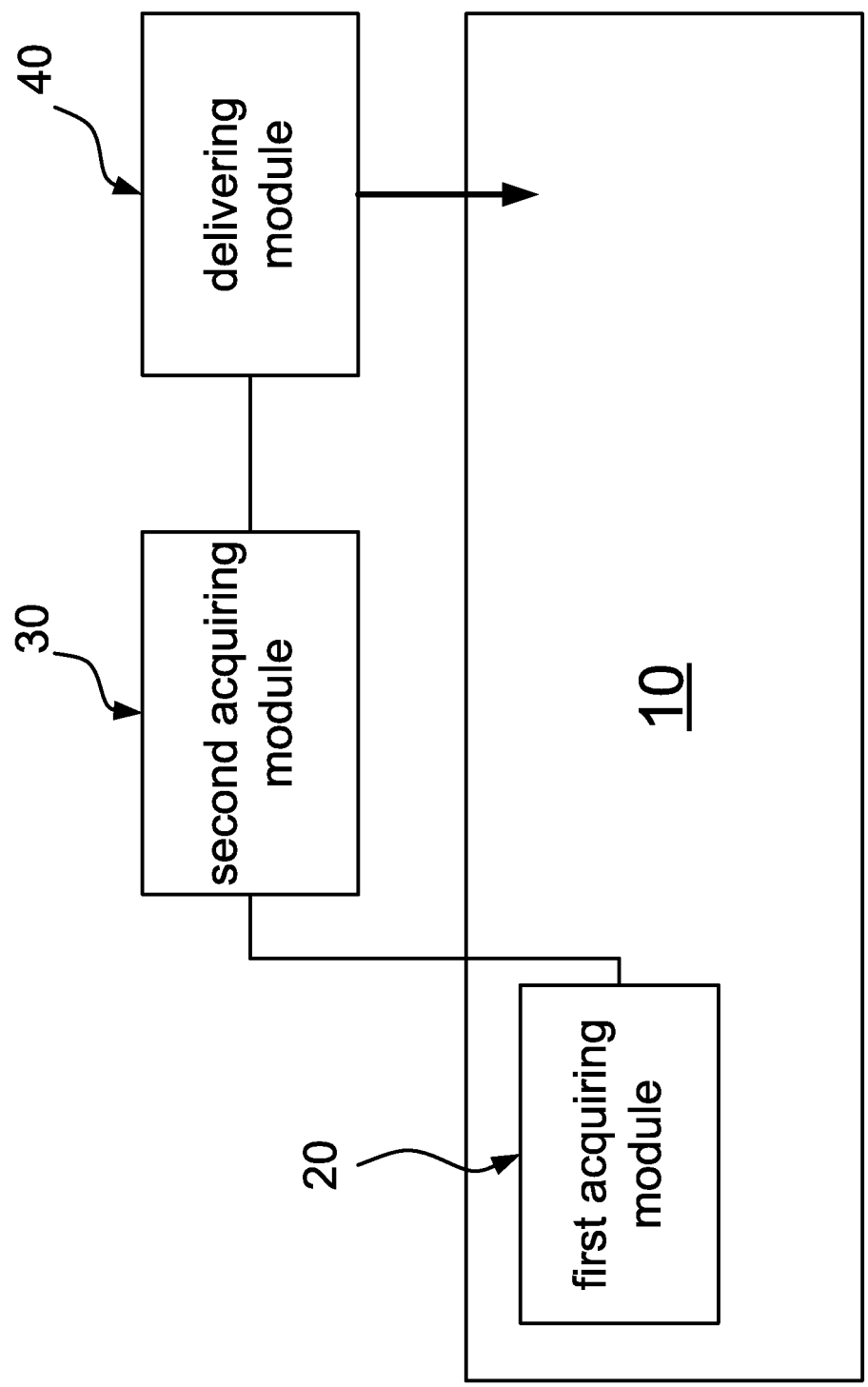
FIG. 3 shows a block diagram of a metal etching control device according to the present invention.
Figure 4:
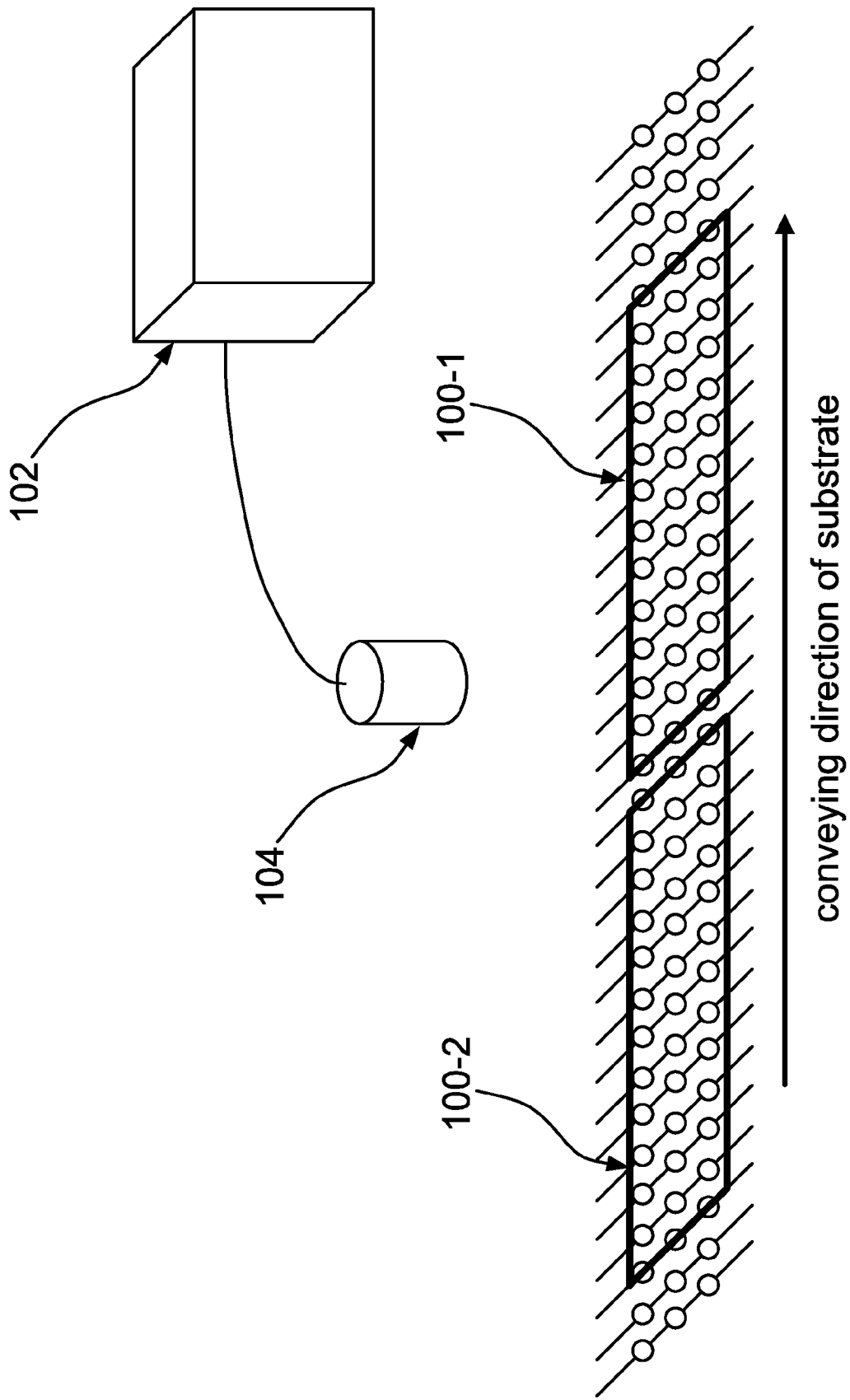
FIG. 4 shows a diagram of that an end point detector is utilized for judging the etching end time in the present invention.
Figure 6:
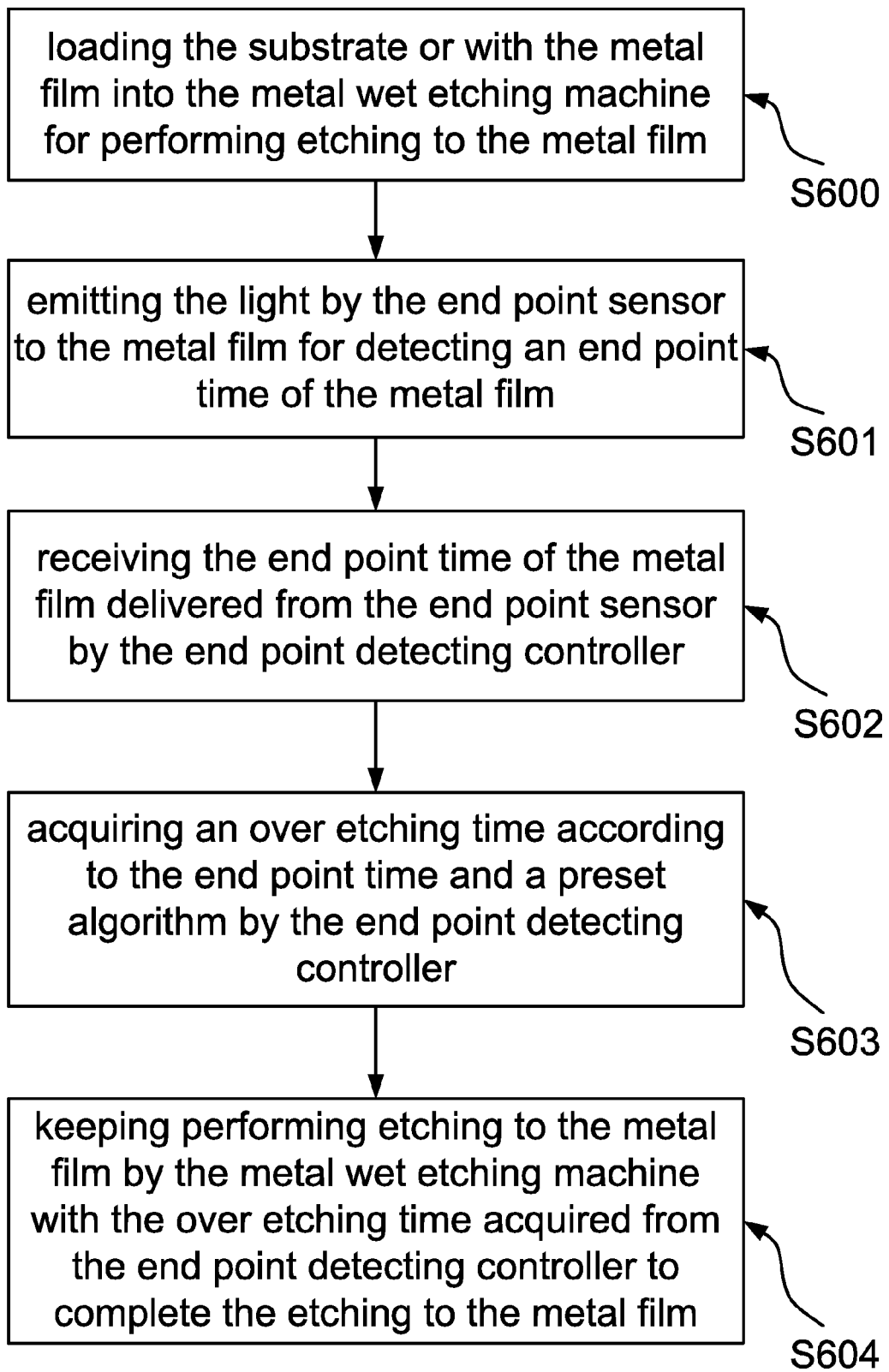
FIG. 6 shows a flowchart of the metal etching method according to the present invention.

Please refer to FIG. 3, FIG. 4 and FIG. 6. FIG. 3 shows a block diagram of a metal etching control device according to the present invention. FIG. 4 shows a diagram of that an end point detector is utilized for judging the etching end time in the present invention. FIG. 6 shows a flowchart of the metal etching method according to the present invention. As shown in FIG. 3, the metal etching control device of the present invention is employed in a metal wet etching machine. The metal etching control device comprises a first acquiring module 10, a second acquiring module 20 and a delivering module 30. The first acquiring module 10 is utilized to acquire an etching end time of the metal film. The second acquiring module 20 is utilized to acquire an over etching time according to the etching end time and a preset algorithm. The delivering module 30 is utilized to deliver the over etching time to the metal wet etching machine. Hereby, the metal wet etching machine keeps performing etching to the metal film with the over etching time to complete the etching to the metal film. The first acquiring module 10 can be an end point sensor 104 as illustration, and the second acquiring module 20 and the delivering module 30 can be an end point detecting controller 102 as illustration but not limited thereto. The first acquiring module 10, the second acquiring module 20 and the delivering module 30 also can be specifically realized by the interior control mechanism of the metal wet etching machine. The end point sensor 104 can be located inside the metal wet etching machine for detecting the etching end time of the metal film carried by each of the substrates 100-1, 100-2 during the etching.

Figure 5:
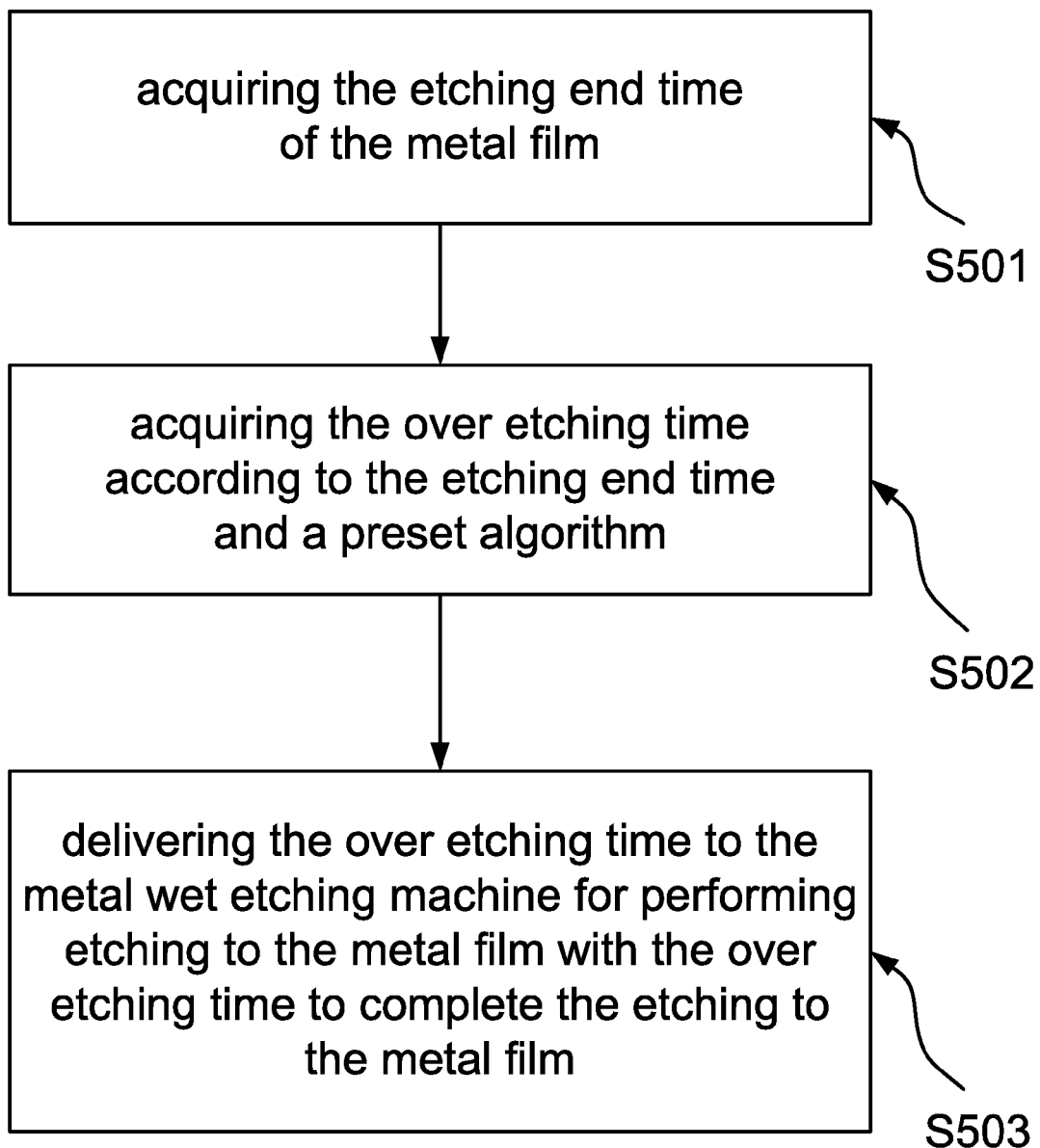
FIG. 5 shows a flowchart of the metal etching control method according to the present invention.

As shown in FIG. 5, as the substrates 100-1, 100-2 carrying the plated metal films on the surfaces thereof are loaded into the etching bath and conveyed in the direction indicated by the arrow in figures, the end point detecting controller 102 controls the end point sensor 104 to emit the light to the metal film, and a receptor of the end point sensor 104 senses whether the light is reflected by the metal film. As the metal film is still under etching, the light generated by the end point sensor 104 is reflected by the metal film because the light cannot penetrate the metal film. As the metal film is completely etched by the acid solution, the light generated by the end point sensor 104 can penetrate the substrates 100-1, 100-2 but not be reflected because the light can penetrate therethrough. Hereby, the end point detecting controller 102 judges that the end point time of the metal film has arrived. The period of time from loading the substrates 100-1, 100-2 into the etching bath till that the end point detecting controller 102 judges the end point of the metal film is just the end point time. Subsequently, the end point detecting controller 102 acquires an over etching time according to the etching end time and a preset algorithm. The metal wet etching machine performs etching to the metal film with the over etching time to complete the etching to the metal film of the substrate 100.

Please refer to FIG. 4 and FIG. 5. FIG. 5 shows a flowchart of the metal etching control method according to the present invention. The metal etching control method employed in the metal wet etching machine is utilizing the metal etching control device shown in FIG. 3 to control the etching to the metal film. In the embodiment of the present invention, the metal etching control method comprises steps below:

Step 501: acquiring an etching end time of the metal film;

Step 502: acquiring an over etching time according to the etching end time and a preset algorithm; and Step 503: delivering the over etching time to the metal wet etching machine to keep performing etching to the metal film with the over etching time to complete the etching to the metal film.

Please keep referring to FIG. 4 and FIG. 6. The metal etching control method employed in the metal wet etching machine is utilizing the metal etching control device shown in FIG. 3. In this embodiment of the present invention, a total real etching time needed for each of metal films can be precisely judged because end point sensor 104 is located inside the metal wet etching machine to detect the etching end time of the metal film of each substrate during the etching.

In this embodiment of the present invention, the metal etching method comprises steps below:

Step 600: loading the substrates 100-1 or 100-2 with the metal film into the metal wet etching machine for performing etching to the metal film;

Step 601: emitting the light by the end point sensor 104 to the metal film for detecting an end point time of the metal film;

Step 602: receiving the end point time of the metal film delivered from the end point sensor 104 by the end point detecting controller 102;

Step 603: acquiring an over etching time according to the end point time and a preset algorithm by the end point detecting controller;

Step 604: keeping performing etching to the metal film by the metal wet etching machine with the over etching time acquired from the end point detecting controller 102 to complete the etching to the metal film.

During Step 603, the end point detecting controller 102 performs the preset algorithm. For example, the end point detecting controller multiplies the etching end time with a constant ratio to acquire the over etching time. And during Step 603, the metal wet etching machine keeps performing etching to the metal film with the over etching time to complete the etching to the metal film. According to the present invention, the issue of unstable etching qualities as the metal film thicknesses are not regular can be reduced. For example, suppose the metal film thickness of the substrate 100-1 is 3000 Å, the acquired etching end time is 100 sec and the ratio of the over etching time is 42%. The end point detecting controller 102 can figure out the etching rate to the metal film of the substrate 100-1 is 30 Å/sec. Then, the over etching time is derived as 42 sec. Therefore, the total real etching time of the metal wet etching machine for the metal film thickness of the substrate 100-1 is 142 sec.

After that, the metal wet etching machine performs etching to the substrate 100-2. For example, suppose the metal film thickness of the substrate 100-1 is 2700 Å, the acquired etching end time is 90 sec and the ratio of the over etching time remains 42%. The end point detecting controller 102 can figure out the etching rate to the metal film of the substrate 100-2 is 30 Å/sec. Then, the over etching time is derived as 37.8 sec. Therefore, the total real etching time of the metal wet etching machine for the metal film thickness of the substrate 100-2 is 127.8 sec. In case that the metal film thickness is thicker than 3000 Å. With the same preset algorithm, the total real etching time of the thicker metal film still can be derived.

Moreover, the concentration of the acid solution in the etching bath degrades with the increased amount of the substrates that the etching process have been performed. According to the performed numbers of the metal film etching, the preset algorithm can be amended by adding the constant ratio of the over etching time with an extra necessary fixed ratio. The extra necessary fixed ratio is obtained from the metal wet etching machine by the end point detecting controller 102 after certain times of the metal film etching; alternatively, an extra linear increasing percentage with the increase of the etching end times can be added; alternatively, an arithmetic series percentage or an geometric series percentage obtained from the experience can be added; alternatively, an error offset needed for rectifying the set ratio of the over etching time can be added as considering the concentration degradation of the acid solution. The error offset is derived from a look up table related with the performed numbers of the metal film etching and the error offset. Furthermore, the preset algorithm can be specifically realized by the interior control mechanism of the metal wet etching machine. For example, the interior control mechanism can perform the aforesaid preset algorithm and the aforesaid rectifications after the metal wet etching machine can receives the etching end time from the end point detecting controller 102 and the end point sensor 104.

Moreover, the preset algorithm can be realized in the end point detecting controller 102 via software or firmware. Because the etching end time of the metal film of each substrate, which is acquired by the end point sensor 104 is feed backed to the end point detecting controller 102, therefore, even the concentration of the acid solution in the etching bath degrades with the increased amount of the substrates that the etching process have been performed, the end point detector of the present invention can precisely control the etching qualities stably and dramatically to promote the yield of the LCD panel manufacture.

Furthermore, only the constant ratio between the over etching time and the etching end time has to be set in advance and to be input into the end point detecting controller 102 according to the present invention. After that, the end point detector of the present invention performs the end point detection and judgment, the metal wet etching machine can spontaneously feed back the etching end time sensed and acquired by end point sensor 104 to the end point detecting controller 102. Then, the end point detecting controller 102 can precisely judge the total real etching time needed for each of the metal film.

As is understood by a person skilled in the art, the foregoing preferred embodiments of the present invention are illustrative rather than limiting of the present invention. It is intended that they cover various modifications and similar arrangements be included within the spirit and scope of the appended claims, the scope of which should be accorded the broadest interpretation so as to encompass all such modifications and similar structure.

What is claimed is:

1. A metal etching method, employed in a metal wet etching machine, wherein the metal etching method comprises steps of:

performing etching to a metal film on a substrate and acquiring an etching end time of the metal film, wherein the etching end time of the metal film is detected by an end point sensor and is a period of time from loading the substrate into an etching bath till that an end point of the metal film is judged by an end point detecting controller;

multiplying the etching end time with a ratio to acquire an over etching time of the metal film, wherein the ratio is a sum of a constant ratio plus an extra necessary fixed ratio, which is presupposed according to metal film etching times performed by the metal wet etching machine; and keeping performing etching to the metal film with the over etching time to complete the etching to the metal film.

2. The metal etching method of claim 1, wherein the step of acquiring the etching end time of the metal film is that the metal wet etching machine acquires the etching end time from the end point sensor.

3. The metal etching method of claim 2, wherein the step of multiplying the etching end time with the ratio is executed by the metal wet etching machine or the end point sensor.

4. The metal etching method of claim 2, wherein the end point sensor is located inside the metal wet etching machine for detecting the etching end time of the metal film during the etching.

5. The metal etching method of claim 1, wherein the ratio is 42%.

6. A metal etching control method, employed in a metal wet etching machine, wherein the metal etching control method comprises:

acquiring an etching end time of a metal film on a substrate, wherein the etching end time of the metal film is detected by an end point sensor and is a period of time from loading the substrate into an etching bath till that an end point of the metal film is judged by an end point detecting controller;

acquiring an over etching time of the metal film according to the etching end time and a preset algorithm, wherein the preset algorithm is to multiply the etching end time with a ratio to acquire the over etching time, and the ratio is a sum of a constant ratio plus an extra percentage, which is presupposed according to the increase of the etching end time; and delivering the over etching time to the metal wet etching machine, so that the metal wet etching machine keeps performing etching to the metal film with the over etching time hereby to complete the etching to the metal film.

7. The metal etching control method of claim 6, wherein the extra percentage is an extra linear increasing percentage, an arithmetic series percentage or a geometric series percentage.

* * * * *